(12) United States Patent
Überreiter

(10) Patent No.: US 6,880,404 B2
(45) Date of Patent: Apr. 19, 2005

(54) SYSTEM ELEMENTS FOR MEASURING PRESSURE IN EXTRACORPOREAL CIRCUITS

(75) Inventor: Andreas Überreiter, Aschaffenburg (DE)

(73) Assignee: MHM Harzbecher Medizintechnik GmbH, Aschaffenburg (DE)

( * ) Notice: Subject to any disclaimer, the term of this patent is extended or adjusted under 35 U.S.C. 154(b) by 27 days.

(21) Appl. No.: 10/332,315

(22) PCT Filed: Jul. 9, 2001

(86) PCT No.: PCT/EP01/07879

§ 371 (c)(1),
(2), (4) Date: Jun. 26, 2003

(87) PCT Pub. No.: WO02/03854

PCT Pub. Date: Jan. 17, 2002

(65) Prior Publication Data

US 2004/0050168 A1 Mar. 18, 2004

(30) Foreign Application Priority Data

Jul. 8, 2000 (DE) .......................................... 100 32 616

(51) Int. Cl.[7] .................................................. G01L 7/00
(52) U.S. Cl. .......................................... 73/706; 73/730
(58) Field of Search .......................... 73/700, 706, 708, 73/730, 716

(56) References Cited

U.S. PATENT DOCUMENTS

| | | |
|---|---|---|
| 3,721,127 A | 3/1973 | Garcea |
| 4,185,641 A | 1/1980 | Minior et al. |

(Continued)

FOREIGN PATENT DOCUMENTS

| | | |
|---|---|---|
| DE | 21 29 670 A | 6/1971 |
| DE | 2129670O S | 12/1971 |

(Continued)

OTHER PUBLICATIONS

Brochure –Disposable Transducer Domes, Specialty Medical Products, Dallas, Texas 1990.

(Continued)

*Primary Examiner*—Edward Lefkowitz
*Assistant Examiner*—Andre Allen
(74) *Attorney, Agent, or Firm*—Baker & Daniels

(57) ABSTRACT

The aim of the invention in particular is to reduce the risk of haemolysis in extracorporeal blood circulation. To this end, a system element for releasably sealingly connecting a transducer to a fluid system comprises a measuring chamber (7) which can be connected to the fluid system in such a way as to allow throughflow. Said measuring chamber (7) is formed in a housing (10). Part of the wall of the measuring chamber (7) is formed by a membrane (11) which is considerably more flexible than the rest of the wall (15) of said measuring chamber (7). The membrane (11) has a peripheral built-up section (20) which is located on the side of the membrane (11) that faces towards the measuring chamber (7). Said built-up section (20) engages in a channel (19) which is formed in the housing (10) and which extends around the measuring chamber (7). The wall (inner wall 16) of the channel (19) that faces towards the measuring chamber (7) is lower than the wall (outer wall 17) of the channel (19) that faces away from the measuring chamber (7) (19). The invention also provides for a system element for releasably sealingly connecting a transducer to a fluid system, containing at least one sensor for converting pressures and pressure changes into electrical signals. The sensor is located in a housing (26) and at least part of the housing (26) is filled with a fluid or gel which transmits pressure. The housing (26) is closed by a transducer membrane (23) on one side. In the area (24) surrounding the transducer membrane (23), the housing (26) is configured for applying one of the system elements (1) according to one of the preceding claims. This surrounding area (24) essentially encompasses the transducer membrane (23) in a ring shape. The measuring range of the sensor has differential pressures of at least −250 mm Hg to +1000 mm Hg in relation to the surroundings. The invention also relates to a set comprising the inventive system elements.

25 Claims, 3 Drawing Sheets

U.S. PATENT DOCUMENTS

| | | | |
|---|---|---|---|
| 4,562,409 A | 12/1985 | Saito et al. |
| 4,562,845 A | 1/1986 | Furst et al. |
| 4,920,972 A | 5/1990 | Frank et al. |
| 5,000,049 A | 3/1991 | Cooper et al. |
| 5,551,300 A | 9/1996 | Vurek et al. |
| 5,614,677 A | 3/1997 | Wamsiedler et al. |
| 5,722,399 A | 3/1998 | Chevallet et al. |
| 6,117,086 A | 9/2000 | Shulze |
| 6,168,653 B1 | 1/2001 | Myers |
| 2001/0000611 A1 | 5/2001 | Cline et al. |

FOREIGN PATENT DOCUMENTS

| | | |
|---|---|---|
| DE | 29 30 869 C2 | 1/1980 |
| DE | 35 25 536 A1 | 1/1987 |
| DE | 42 19 888 A1 | 1/1994 |
| DE | 9317751 U1 | 3/1994 |
| DE | 44 19 593 A1 | 12/1995 |
| EP | 0 330 891 B1 | 11/1992 |
| EP | 0 701 830 A1 | 3/1996 |
| EP | 0 878 628 A2 | 5/1998 |
| GB | 2 029 579 | 3/1980 |
| WO | WO 97/39679 | 10/1997 |
| WO | WO 99/37983 | 7/1999 |

OTHER PUBLICATIONS

Brochure –Sensonor 840, SensoNor A.S., Horten Norway.
Extract from a standard text publication in the field of cardiology, Beitrage Zur Kardiologie, Band 29, author R. Buchwalsky, pp. 104–109, 1985.

SYSTEM ELEMENTS FOR MEASURING PRESSURE IN EXTRACORPOREAL CIRCUITS

This application is a 371 of PCT/EP01/07879 Jun. 9, 2001.

The invention relates to a system element for the releasable sealed connection of a transducer to a fluid system, with a measuring chamber which can be connected to the fluid system in such a way as to allow throughflow, the measuring chamber being formed in a housing and part of the wall of the measuring chamber being formed by a membrane which is considerably more flexible than the rest of the wall of the measuring chamber, and also a system element for the releasable sealed connection of a transducer to a fluid system, containing at least one sensor for converting pressures and pressure changes into electrical signals, the sensor being arranged in a housing and at least part of the housing being filled with a fluid or gel which transmits pressure, and the housing being closed by a transducer membrane on one side, the housing being further configured in the area surrounding the transducer membrane for applying one of the system elements as claimed in claim 1, the surrounding area essentially encompassing the transducer membrane in a ring shape, and a set comprising such system elements.

Such connecting elements are known in medical technology by the colloquial term "dome" or "pressure dome", which originates from the dome-shaped design of the measuring chamber, or by the term "transducer", which is understood as meaning a measuring converter in a suitable housing which converts the pressures and pressure changes usually transmitted via the membrane of the pressure dome into an electrical signal. They serve the purpose of permitting the measurement of pressures in fluids during the examination and treatment of people and animals, preferably by means of electronic diagnostic and monitoring equipment.

DESCRIPTION OF THE PRIOR ART

For pressure monitoring during the flushing of body cavities, in DE 42 19 888 A1, for example, there is described a flow pressure transducer with such a connecting element, which is designed for a large volume throughput in accordance with the intended area of use. At the same time, the flow pressure transducer is to be designed as a pressure-relief valve which bypasses a peristaltic pump when the differential pressure predetermined by the structural design of the flow pressure transducer on the pressure side of said peristaltic pump with respect to the suction side of the pump is exceeded.

For monitoring the hemodynamic parameters of a patient, in particular intensive-care patients, it is customary nowadays in addition to the recording of an ECG also to record the invasive pressures into the [sic] patient monitoring, that is to say keeping a check on the state of the vital bodily functions of the patient. Depending on the degree of monitoring, between one and four pressures (arterial, pulmonary-arterial, LAP and venous) are measured.

For this purpose, a catheter with an integrated monitoring set is used. The positioning of the end opening of the catheter defines the measuring point in the patient's body. A monitoring set refers to a compilation of those parts which establish the connections between the patient and the so-called monitor and, usually for reasons of hygiene, are intended for once-only use. A monitor refers to the electronic monitoring and recording system with which the corresponding measured data are evaluated and displayed, and which if need be emits corresponding alarm signals if measured data leave prescribed set ranges.

A general description of this, relating to the example of examination by a flow-directed catheter, is found in Buchwalsky, Rainer: Einschwemmkatheter: Technik, Auswertung u. prakt. Konsequenzen [flow-directed catheters: technology, evaluation and practical consequences] (Beiträge zur Kardiologie [articles on cardiology], Vol. 29); Erlangen: perimed Fachbuch-Verlagsgesellschaft, 1985, pages 106–109.

The monitoring set to be fastened to the catheter comprises an unventilated infusion apparatus for feeding infusion solutions to the patient, a flushing system, which ensures a continuous flushing rate of customary 3 ml/h at the catheter tip to avoid occlusion being caused by thrombi, if appropriate with a quick flushing function for special cases, and a pressure dome. The pressure dome transmits the pressure signal via its flexible membrane to a reusable transducer (pressure sensor). Such a pressure dome has in the past been fastened on such a transducer by a screw or bayonet connection (see in this respect DE 42 19 888 A1, column 3, lines 28 to 30), or by means of snap hooks (cf. WO 99/37983).

Examples of such pressure domes are to be found on an information sheet "Disposable Transducer Domes" of the company SMP Specialty Medical Products, Dallas, Tex., US, with reference to the models 078 to 082. A typical transducer (pressure sensor) is described, for example, in a leaflet of the company SensoNor a.s, Horten, NO, Edition 1/95, on the product SensoNor 840.

Further elements of a monitoring set are the pressure hoses (marked in color) and possibly a three-way cock, to allow medicaments to be fed in, or a blood removal system for taking blood for further investigations.

A special problem is that of venting the parts of the monitoring set in connection with the blood system. The problems involved in venting such systems are generally known to the users. During the filling of the system (usually with physiological saline solution), air bubbles become trapped particularly easily in the dome, i.e. in its dome-like measuring chamber above the membrane. On account of the great elasticity inherent in gases, by contrast with the virtually incompressible fluids, the air bubbles trapped there represent a barrier in the transmission of pressure frequencies of more than a few Hertz. This has the effect of significantly falsifying the transmission of the change in pressure to the membrane, and consequently to the transducer lying thereunder, and as a result the representation of the pressure curves on the monitor.

A connecting element of the type mentioned at the beginning is known from prior public use by SMP Specialty Medical Products, Dallas, Tex., US, under the type designation 081. This "dome" is intended to fit the Hewlett Packard 1290 Quartz transducer and allow itself to be fastened on the latter by means of a bayonet connection. Lockable Luer-lock connections with a loose threaded part, or with an external full thread, as are specified for example in DIN 13 090 Part 2, serve for connecting the inlet channel and outlet channel to the hoses of a monitoring set.

The known connecting element is produced from a crystal-clear plastic. The measuring chamber of this connecting element is very large and has, in particular, a large diameter of approximately 23 mm. In this case, the ceiling of the measuring chamber is at the same time the upper side of the housing. This ceiling and upper side of the housing is formed in a plane-convex manner as a magnifying lens. This is intended to achieve the effect that even small bubbles in the measuring chamber are detected as reliably as possible by the medical care personnel.

Disposable transducers which contain the pressure-measuring sensor in a flow housing are therefore designed in the form of a simple tube in the flow chamber in order to avoid this very trapping of air bubbles. However, they have the disadvantage that the valuable electronics are integrated in the disposable article and therefore are thrown away each time the monitoring set is changed and have to be disposed of along with it. To comply with hygiene requirements, such an exchange must take place at the latest every second day. This entails not only the disadvantage that the still serviceable electronics are replaced with every change, accompanied by corresponding costs, but also that the presence of electronic components requires additional special, and consequently cost-intensive, treatment as electronic scrap during disposal.

For this reason, dome systems which can be used repeatedly are becoming more popular, at least in Europe. The valuable electronics, in particular the pressure sensor, are located in a special housing. Such a part is usually referred to as the transducer. One or more transducers are integrated in a special retaining plate. The retaining plate is fastened, for example on an infusion stand, by means of a clamping or screwing device. The measured pressure data are transmitted from the transducers in the retaining plate to the monitor via one or more cables.

This problem is also not solved by a connecting element of the type mentioned at the beginning, such as that described in DE 35 25 536 A1. To avoid damage, in particular to the membrane of the connecting element, a fastening in which it is not necessary for the connecting element and transducer to be turned in relation to one another is proposed there. For this purpose, additional fastening elements, such as pivotably mounted clamps or closing hooks elements, are to be provided at two points on the circumference of the housing of the connecting element.

It is proposed there to allow these fastening elements or continuations to protrude downward beyond the membrane for the handling of the fastening elements. This is intended to make it possible to check visually that locking of the fastening element provided has also been carried out. Furthermore, this is intended to simplify handling when the connecting element is removed from the transducer. However, it practically rules out a combination with transducers fastened in retaining plates.

Furthermore, according to the teaching of this printed publication, the housings of the pressure dome and transducer are intended to touch one another directly (see column 9/10 therein), whereby the membranes of the pressure dome and transducer are indeed intended to lie "snugly on each other", but prestressing of the membranes is considered disadvantageous and is to be avoided (loc. cit., column 4, lines 21 et seq.).

EP 0 701 830 A1 describes a device and a method preferably for use in the area of pressure measurement in blood-carrying lines for dialysis equipment, for hemofiltration and hemodiafiltration. For this purpose, the pressure is measured indirectly via a gas column (air), which is in connection with the liquid column in a line via an elastic membrane located in a housing. The pressure of the gas column is registered by means of suitable and customary sensors (pressure pickups). To extend the restriction of the measuring range caused by the mechanically limited deflectability of the membrane and the compressibility of the gas column, there is proposed a device and a method with which the amount of gas in the gas-carrying part of the measuring instrument is increased or decreased in dependence on the gas pressure to be measured and with the result of maintaining mobility of the membrane and consequently the relaying of changes in pressure.

Changing the amount of gas takes place by means of pumping devices in the form of a peristaltic pump actuated by means of a control system. The compressibility of the volume of gas to be interposed according to the EP application has the effect of forming a kind of acoustic low-pass filter, which damps or suppresses rapid changes in pressure or relatively high-frequency pressure oscillations. The system according to the printed publication is suitable in practice only for measuring static pressures or for monitoring mean values, it being possible to set the formation of the mean pressure value by the damping characteristics of the system, for example by means of the volume of gas switched between the membrane and pressure transducer. For arrangements of such a type, an upper cut-off frequency of approximately 0.1 Hz is known from prior use for registering changes in pressure.

The publication also describes in detail a method with modifications as to how the desired setting of the position of the membrane, and consequently of the measuring range, can take place without the position of the membrane having to be registered mechanically or observed by using an electronic control system through successive increasing and decreasing of the amount of gas in the gas-filled part of the system.

Disclosed in the publication is a pressure-measuring device with a pressure transducer (38) which is sensitive to changes in a gas pressure and is connected via an air-filled line (37) to a housing (30). The latter is subdivided by a flexible membrane (33) into two chambers (31, 32), the first chamber (31) being intended to have at least one opening for feeding in liquids.

The second chamber (32) is intended to be connected to the line (37) in a gastight manner via a pipe connection and consequently capable of being connected to the pressure transducer (38).

DE 29 30 869 C2 describes a pressure measuring capsule for fastening on a measuring transducer, which capsule has a housing in which there is formed within an annular bead a hollow space which is closed by the membrane adhesively attached onto the annular bead. It is intended that the hollow space can be filled with a liquid or a gas via two connection tubes.

The main subject-matter of the description is the formation of continuations of a cylindrical housing body of the pressure measuring capsule to form a bayonet connection with correspondingly formed counterparts on a measuring transducer. Emphasized in particular is an elastic design of the continuations to form defined snap-in end positions of the mating parts of the bayonet connection, the pressure transducer and pressure-measuring capsule having to be turned in relation to one another to establish the mechanical connection. For the resilient design of the parts of the bayonet connection on the side of the pressure-measuring capsule, it is intended that production tolerances can be compensated and a snap-in end position of the pressure measuring capsule in relation to the pressure transducer can be achieved.

The snap-in end position is at the same time intended to have the effect of exerting a defined prestressing force on the pressure transducers, the inventors envisaging that said position is to be consistently reproducible with different pressure transducers in such a way that zero balancing of the evaluation electronics used is no longer required.

The cited publication describes a bayonet connection as particularly advantageous, the known disadvantages of which is [sic] in particular a rubbing relative movement between the mating parts to be connected of the bayonet connection.

European Patent EP 0 330 891 B1 describes an arrangement for transmitting the pressure of a fluid to another fluid. Proposed for this purpose is an elongate housing, the inner space of which in the form of an ellipsoid of revolution is divided into two spaces by a flexible membrane, it being possible for these two spaces to be arranged in such a way that they form respectively neighboring areas of the inner space, or else concentrically. One of the spaces is intended to be provided with an inlet opening and an outlet opening, to allow a first fluid to flow through it, such as blood for example.

The second space is provided with a single opening, via which a fluid which can be introduced into the second space is to be connected to an external pressure-measuring device, for example, in order for instance to measure the pressure of the blood which is flowing through the first space.

It is described and claimed as essential for the invention to introduce the membrane into the housing in an unstretched or even folded state, the inventors concerned hoping that this brings about an improvement in the pressure-measuring capabilities and in particular the measurement also of negative pressures, without any further details of this being specified.

WO 97/39679 describes a coupling of a kind of pressure dome with a transducer, although the measuring chamber of the "pressure dome" is not closed off from the surroundings by a membrane but by an isolating gel. When the pressure dome and transducer are being fitted, the flowability of the gel is intended to make it possible for air between the pressure dome and transducer to be pressed out through venting channels.

U.S. Pat. No. 4,562,845 describes a screw connection which leads to a sealed coupling of a pressure dome to a transducer. Since the device described there is intended to be part of the system likewise described there for monitoring other transducers for a malfunction and for registering air bubbles in blood-pressure monitoring systems, the pressure dome described there does not have a membrane for the sterile sealing of the fluid system from the surroundings and the transducer.

U.S. 4,462,409 discloses a pressure dome which, however, is not intended for looping into an extracorporeal circulation or for an infusion solution to flow through but as a termination of a tap line which can be hydraulically coupled via an infusion system to the circulation of a patient for pressure transmission. The measuring chamber of this pressure dome is separated from a transducer by means of a membrane. The transducer comprises a two-part housing, a first housing part (53 there) has a connecting area for the membrane of the pressure dome to be applied. Provided on this connecting area of the housing part is a rib (63a), which is intended to ensure a firm fit of a bead of the membrane in a groove in the housing and consequently ensure reliable sealing of the measuring chamber.

However, the pressure dome is firmly connected to the housing part of the transducer by welding (loc. cit., column 4, lines 60–67), so that an arrangement with a disposable dome and a reusable transducer is not possible.

U.S. Pat. No. 4,9200,972 [sic] describes a system comprising a disposable dome and a reusable transducer in which the measuring chamber in the dome and also the transducer are respectively closed off by means of a membrane. Moreover, the teaching of this printed publication is concerned with the replacement of oil for pressure transmission within the transducer by a gel, that [sic] only sets to the desired gel form after it has been introduced in liquid form into the transducer housing, by heating up the transducer to 65° C. throughout for four hours. This arrangement is intended to increase the upper cut-off frequency of a transducer.

U.S. Pat. No. 5,551,300 discloses a set comprising a disposable pressure dome and a reusable transducer in which both the measuring chamber of the pressure dome and a liquid-filled measuring space of the transducer are closed off by a flat membrane adhesively attached to the respective housings. In this case, it is intended in respect of the transducer for a pressure equalization of the liquid-filled measuring space of the transducer to be carried out in such a way that the measuring space is in flow connection with an equalization vessel, which is closed off from the surroundings by means of an elastic membrane.

The liquid system is in this case to be filled with a slight positive pressure, in order to ensure contact of the two pressure-transmitting membranes and consequently the operational capability of the system. To prevent a pressure equalization in the liquid system of the transducer during the measurement, which is a prerequisite for pressure measurement, it is proposed to allow the transducer membrane to protrude slightly and to provide a connection of the liquid-filled measuring chamber of the transducer to the pressure-equalizing vessel via a hole on the front side of the transducer, which is likewise covered by the transducer membrane. By connection with the pressure dome, the membrane is mechanically applied to the housing of the transducer and, as a result, the equalizing opening is closed, so that only the liquid remaining in the measuring chamber of the transducer can damp a signal transmission to a piezo sensor.

DE 44 19 593 A1 discloses a device for measuring the pressure of a medium, in particular for pressure measurement in extracorporeal blood circulations, for example a dialysis system, in which a disposable element which contains a measuring chamber and has two hose connections is provided, it being intended for the measuring chamber to be closed by a membrane which is to be placed in a peripheral groove and fastened there by means of a metallic clamping ring or by adhesive bonding. It is emphasized there as being particularly expedient that a peripheral bead is formed around the part of the measuring chamber which is in connection with the membrane, in particular by an O-ring, which raises the membrane in the area of the connection to the measuring chamber above the surface of the element. This is intended to make it possible to obtain good coupling of the membrane to a pressure-measuring transducer when the element is placed into a drawer of the measuring system and the pressure transducer is moved toward the element, preferably pneumatically or by means of a spindle.

However, in comparison with the prior-art pressure systems described further above, it should be emphasized that the element does not vent itself and that numerous gaps and niches in which air bubbles can easily collect during the filling of the system remain, in particular in the area between the connecting opening to the measuring chamber and the surrounding bead under the membrane. As already stated further above, not only is this disadvantageous with regard to the quality of the pressure transmission or the blood pressure measurement, but there is also the considerable risk of clotting of the blood or the formation of blood clots, which can, in particular in the case of extracorporeal blood circulations, be life-threatening to the patient if such blood clots are not intercepted before the blood is fed into the body.

This publication correspondingly does not contain any further details on the measuring range of the system or the quality of the measurements, in particular with respect to the cut-off frequency range, which would allow conclusions to be drawn concerning damping of the system by air bubbles remaining in the measuring chamber.

Furthermore, the device according to DE 44 19 593 A1 requires a considerable amount of effort for the measuring element to be fitted, in particular with regard to the fitting of the membrane, which additionally leads to a great effort being required with regard to checking how well it has been fitted for reasons of product liability. Furthermore, the large number of parts and, in particular, the hollow spaces formed between the membrane and the O-ring can also lead to problems in sterilization. With regard to the effort required for fitting and quality assurance, this leads to such high costs that such a measuring system is not acceptable for disposable use.

Furthermore, the corresponding arrangement of the pressure-measuring sensor requires great expenditure on apparatus, in particular with regard to the moving device for the sensor and the calibration of the sensor, dependent on the path of movement, so that such a system is unsuitable for everyday clinical use on account of the handling effort and enormous costs.

DT 21 29 670 A discloses what is known as a vacuum capsule, in which an elastic membrane is arranged in a fixed metal capsule, aspects described as essential for the invention being the design of the membrane and fastening on a push rod, so that the membrane is applied to one side of the capsule during production and, after prestressing by a spring in dependence on the absolute air pressure to which the membrane is subjected on one side, can perform adjusting work via the push rod and thereby travel over a considerable fixed distance, in particular in dependence on the prestressing by means of the spring. However, this device is not intended to allow throughflow and, on account of the design and intended purpose, is entirely unsuitable for measuring pressures, in particular in extracorporeal circulations.

DE 93 17 751 U1 discloses a pressure-indicating device that [sic] on reaching a certain predetermined pressure value indicates by a color change from green to red, or vice versa, visible through a transparent plate, and/or can actuate an electrical switch or button via a push rod. For this purpose, a liquid is enclosed in the intermediate space between a membrane and a measuring housing. If the pressure on the other side of the membrane, which corresponds to the evaporation point of the liquid, falls below a limiting pressure, the liquid evaporates and the membrane abruptly travels together with a push rod fastened to it over a fixed distance, so that a warning button or the like can be actuated by the push rod. Appropriate coloring of the liquid obscures the view through to a plate of a signalling color on the membrane, which suddenly becomes visible when the liquid evaporates and is consequently intended to produce a signalling effect.

It is quite evident that this device is not suitable for the continuous measurement of pressures.

Finally, WO 99/37983 discloses a pressure dome which is designed and suitable in particular for use in extracorporeal blood circulations, for example in hemodialysis, which furthermore can be handled particularly well as a result of a releasable snap connection for fastening on a transducer.

SUMMARY OF THE INVENTION

The invention is therefore based on the object of providing a connecting element of the type mentioned at the beginning which has improved properties with regard to its application-related reliability on the one hand and its handling on the other hand, and also makes it possible for patients to be treated more safely and at lower cost.

This object is achieved according to the invention by a system element of the type mentioned at the beginning in which the membrane has a peripheral bead which is located on the side of the membrane that faces toward the measuring chamber, the bead engaging in a groove which is formed in the housing and extends around the measuring chamber and the wall (inner wall) of the groove that faces toward the measuring chamber being lower than the wall (outer wall) of the groove that faces away from the measuring chamber.

The object is also achieved according to the invention by a system element of the type mentioned at the beginning in which the measuring range of the sensor covers at least differential pressures with respect to the surroundings of −250 mm Hg to +1000 mm Hg.

The object is finally achieved by a set of system elements according to the invention.

The design according to the invention makes it possible for the first time to measure negative pressures in blood circulations to a greater extent than can be produced by the pumping capacity of the heart alone. Furthermore, it is possible for the first time to measure directly in blood circulations negative pressures which are greater than that at which red blood corpuscles in human blood break up under prolonged exposure (hemolysis). Furthermore, it is possible for the first time to register rates of pressure rise so high that adequately rapid automatic control of peristaltic pumps connected in series is possible, so that the duration of the effect of a negative pressure on red blood corpuscles can be kept below a critical limit.

In medical technology, extracorporeal circulations are being used to a greatly increasing extent for the life-preserving function in critical areas, such as open-heart surgery, multi-organ failure in cases of infections or accidents, detoxification by hemofiltration, for treatment in the case of chronic renal insufficiency (hemodialysis) and also for obtaining blood preparations by cell separation. These extracorporeal circulations are operated by usually up to 4 pumps, in most cases peristaltic pumps, the pumps often being used in pairs in series connection.

The pump heads of machines of extracorporeal circulations cannot serve the pump hose segments uniformly enough, so that positive and negative pressures occur in the hose system, in particular if the pump arranged downstream starts up quicker than the upstream pump. Under some circumstances this produces a negative pressure for just fractions of a second in the area of the line between the pumps. The constituents of the blood are very sensitive to negative pressures; the red blood corpuscles may break up and hemolysis occurs. To avoid critical pressure ranges, nowadays T-pieces are looped in and pressure transducers on PC boards are used via tap lines and hydrophobicized filters with connected air lines. This solution is so slow on account of the elastic buffer volumes that the critical pressure ranges are not avoided, at least for a short time, and consequently negative pressures down to −300 mm Hg nevertheless occur as pressure peaks in the range of a few seconds.

With the arrangement according to the invention, pressure changes in the negative pressure range down to −400 mm Hg can be registered up to the cut-off frequency $f_G$ of approximately 60 Hz. This is achieved, inter alia, by it being possible for the membrane of the pressure dome to be coupled to the transducer membrane in such a way that it is sufficiently free of air and penetration of ambient air between the coupled membranes being sufficiently prevented by the design according to the invention, so that the pressure transmission to the transducer takes place sufficiently accurately even in the negative pressure range.

In a particularly preferred embodiment, the system element according to the invention is characterized in that the difference in height of the outer wall with respect to the inner wall of the groove is less than the average thickness of the membrane in the area outside the peripheral bead. As a result, a particularly good sealing effect with the transducer housing is achieved, in particular if the membrane protrudes at least approximately 0.1 mm, preferably at least approximately 0.3 mm, beyond the walls of the groove in the area of the bead after insertion of the bead into the groove.

By pressing the membrane against the inner wall of the dome, air bubbles possibly located in the area of the groove can no longer have adverse effects by damping the signal or the negative pressure, nor can they cause clotting of the blood.

The membrane is expediently produced from an EPDM. It may, however, also be advantageous, in particular with regard to the sealing properties, if the membrane is produced from a TPE, in particular if the membrane is produced from a TPE of the class SEBS.

For the use according to the invention, it is particularly expedient if the membrane seals a negative pressure of 530 hPa with respect to air when a pressing pressure of 60 N is applied to a finely turned steel surface.

Falsifications of the measurement due to the stiffness of the membrane can be largely ignored if the membrane has within the bead a diameter of at least 12 mm.

Particularly good fastening of the membrane can be obtained if the bead has a width of approximately 2 mm in the longitudinal extent of the membrane.

A good compromise between transmission properties and production expenditure and also good mechanical durability of the membrane is obtained if the membrane has within the bead a thickness of approximately 0.4 mm to approximately 0.5 mm.

In an expedient embodiment of the invention, the measuring range of the sensor reaches at least down to differential pressures with respect to the surroundings of −350 mm Hg; it is preferred for the measuring range of the sensor to cover at least differential pressures with respect to the surroundings of −400 mm Hg to +3000 mm Hg.

The sealing integrity required for the measurement of negative pressures can be obtained if the surrounding area is approximately technically plane and the surface of the surrounding area is smoothed to make it essentially free of scratches, preferably finely turned, ground or polished, in particular if the surface of the surrounding area has an averaged peak-to-valley height $R_z$ of no more than 20 μm (for example in accordance with DIN 4768 Part 1) and/or the surface of the surrounding area has a maximum peak-to-valley height $R_{max}$ of no more than 30 μm, preferably no more than approximately 20 μm.

When the pressure dome and transducer are put together, the inclusion of even extremely small air cushions can be largely avoided if the transducer membrane is slightly pre-curved with respect to the area surrounding it, in particular if the transducer membrane is pre-curved with respect to the area surrounding it by no more than 1 mm, preferably no more than 0.6 mm.

Particularly good measuring results can be obtained if the transducer membrane is formed from an RTV silicone. It may also be advantageous for improving the long-term stability, however, if the transducer membrane is formed from a polyurethane, preferably a TPE polyurethane.

The sealing integrity required for the measurement of negative pressures can be obtained particularly reliably if the surrounding area has a width of at least 2 mm.

In a preferred configuration, the set according to the invention is characterized in that at least one coupling device for the mechanical connection of the pressure dome and the transducer is provided and the membrane of the pressure dome is pressed in the area of the bead against the area surrounding the transducer membrane, so that an airtight seal takes place between the membrane of the pressure dome and the transducer when the pressure dome and transducer are coupled, in particular if, when coupling has taken place, the membrane of the pressure dome is pressed in the area of the bead with at least 50 N, preferably by 90–110 N, against the area surrounding the transducer membrane, and/or, once coupling has taken place, the membrane of the pressure dome is pressed together in the area of the bead by approximately 0.1 mm to approximately 0.3 mm.

BRIEF DESCRIPTION OF THE DRAWINGS

The invention is to be explained in more detail below on the basis of exemplary embodiments represented in the drawings, in which.

Figure 1:
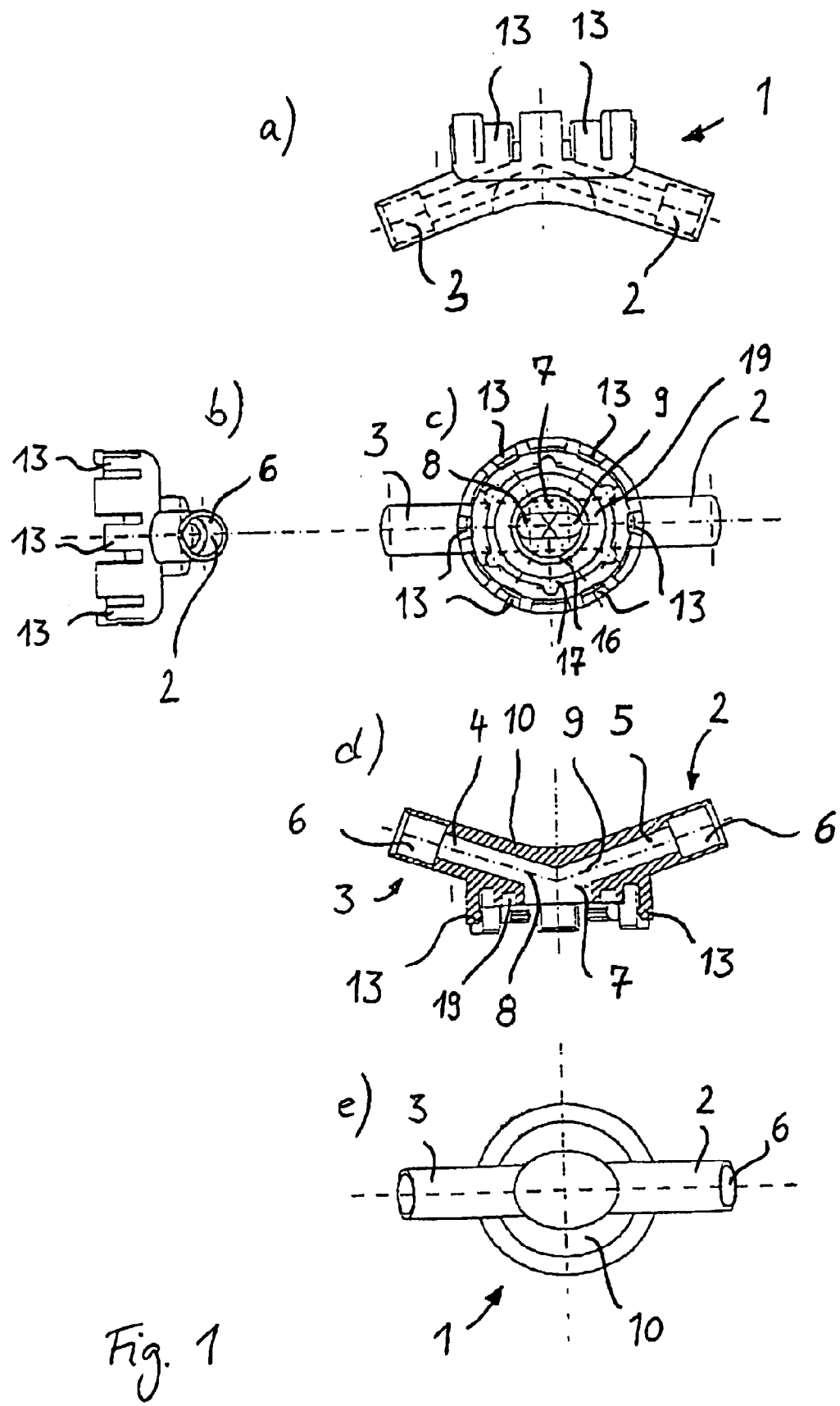
FIGS. 1a–1e show a pressure dome according to the invention in various views.

The system element represented in FIGS. 1a to 1e for the releasable sealed connection of a transducer to a fluid system in the form of a pressure dome 1 has two connections 2, 3 for the connection to an infusion apparatus and to a patient, for example via a cemented-in three-way cock, or for looping into an extracorporeal blood circulation, for example a dialysis apparatus, a heart-lung machine or a cell separator. The connections 2, 3 respectively have a channel 4, 5, preferably with a conical packing seat, a cementing-in groove or some other sealed connection system 6 customary in medical technology. The dimensioning of the connections 2, 3 may conform for example to DIN 13090.

Connected to the inlet channel 4 and the outlet channel 5 via an inlet opening 8 and an outlet opening 9 is a measuring chamber 7, so that a flow path from the inlet channel 4 through the measuring chamber 7 into the outlet channel 5 is obtained.

The measuring chamber 7 is formed in a housing 10, which is produced as a one-piece injection-molded part, preferably from a transparent plastic, for example a polycarbonate. Part of the wall of the measuring chamber 7 is formed by an elastic membrane 11 (omitted in FIG. 1), for example of an EPDM, a TPE, preferably of a TPE of the class SEBS, or some other suitable material that is resistant to blood and/or infusion solution and is physiologically harmless. Consequently, the connecting part preferably comprises merely the membrane 11 and a one-piece plastics injection-molded part.

The material of the membrane and its processing, for example injection molding, during production should create a membrane which seals a negative pressure of 530 hPa with respect to air when a pressing pressure of 60 N is applied to a finely turned steel surface.

At the height of the membrane 11 there is further provided a device for the mechanical coupling of the connecting element to the transducer (12) which is part of a releasable spreading-in connection, which is formed by claw-shaped retaining elements in the form of hooks 13 for engagement in a corresponding groove or undercut 14 of the transducer 12 or an associated fastening device.

The hooks 12 are formed by resilient continuations of the housing 10 and preferably six of them are evenly distributed over the circumference of the pressure dome 1. In this arrangement, the resilient connection of hooks 12 to the housing 10 is designed such that a pre-stressing force of at least approximately 60 N can be maintained.

Figure 3:
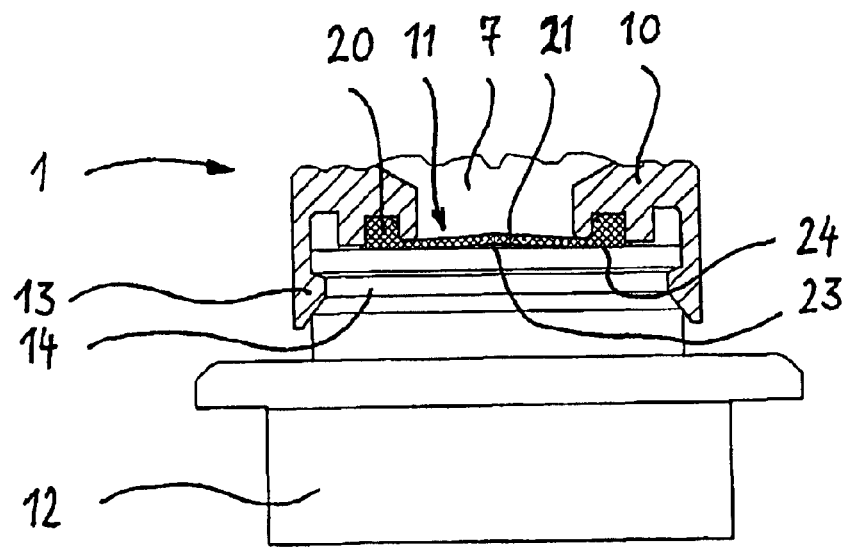
FIG. 3 shows a set according to the invention comprising a pressure dome and a transducer in a partially sectional view.

As can easily be seen in FIG. 3, the pressure dome 1 can be placed onto the transducer 12 by simply pressing on the transducer 12 in a direction approximately perpendicular to a plane which is defined by the membrane 11.

The measuring chamber 7 is bounded radially outward by part of its wall forming an edge 15, the inlet opening 8 and outlet opening 9 butting against this edge 15. In between and opposite the membrane 11, a ceiling (not represented) of the measuring chamber 7 is formed by part of the wall.

Near the membrane 11, the edge 15 is formed by an inner wall 16, which together with an approximately 0.5 mm higher wall (outer wall 17) that faces away from the measuring chamber and a base 18 forms a groove 19 which extends around the measuring chamber 7.

For fastening the membrane 11, a bead 20 which runs around the edge of the membrane 11 and is located on the side of the membrane 11 that faces toward the measuring chamber 7 is pressed into the groove 19. The bead 20 of the membrane 11 may have a width of approximately 2 mm, measured in the longitudinal extent of the membrane 11. The planar area of the membrane 11 within the bead edge 20 expediently has a diameter of at least 12 mm, with a suitable thickness in this area of approximately 0.4 mm to approximately 0.5 mm.

The dimensioning of the inner wall 16 in relation to the depth of the groove 19 is in this case performed in such a way that, after pressing the bead 20 into the groove 19, the flat area 21 of the membrane lifts up from the inner wall 16 by a minimal gap. When the pressure dome 1 is coupled to the transducer 12, the gap is closed without the membrane 11 deforming to any appreciable extent, thereby preventing the membrane 11 from arching up.

Figure 4:
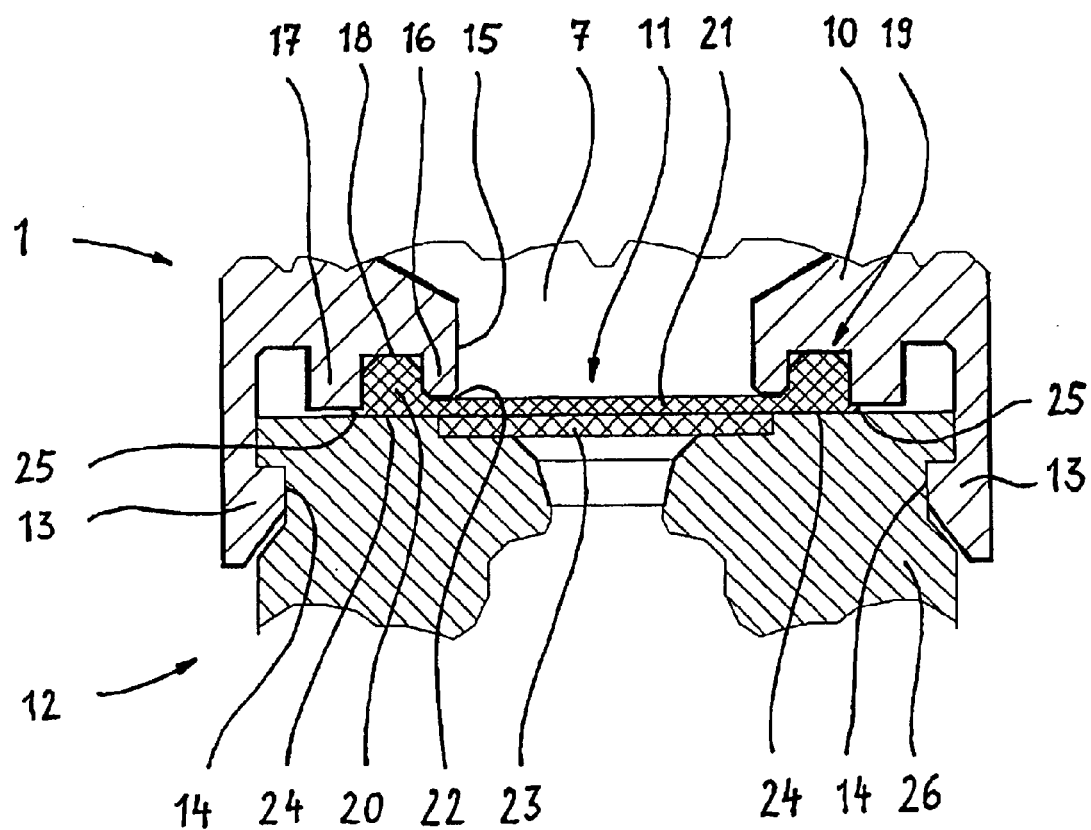
FIG. 4 shows an enlarged detail of the representation according to FIG. 3 as a sectional view.

The difference in height of the outer wall 17 with respect to the inner wall 16 is less than the average thickness of the flat area 21 of the membrane. The height of the outer wall 17 is in this case expediently fixed in such a way that the membrane 11 protrudes at least approximately 0.1 mm, preferably at least approximately 0.3 mm, beyond the outer wall 17 of the groove 19 in the area of the bead 20 after insertion of the bead 20 into the groove 19. When the pressure dome 1 is placed onto the transducer 12, the membrane 11 is slightly squeezed in the area of the bead 20, whereby a kind of sealing lip 25 against air penetrating from the outside is formed (FIG. 4) in the area of the gap 22 which is produced between the outer wall 17 and the corresponding abutment on the transducer 12, the area 24 surrounding the transducer membrane 23.

For use of the connecting element according to the invention in blood-carrying systems, for example in dialysis, the inlet channel and/or the outlet channel 5 is arranged inclined with respect to a plane parallel to the membrane 11. It is advantageous in this case if the inclination of the inlet channel 3 and/or of the outlet channel 5 with respect to a plane parallel to the membrane 11 is approximately 15° to 45°, preferably 15° to 30°, particularly preferably approximately 20°. As a result, the forces on cells present in the fluid when it flows through the connecting element can be minimized. In this way, the risk of a hemolysis, that is breaking up of the red blood corpuscles, can be avoided to the greatest extent by the flow in the pressure dome alone.

Figure 2:
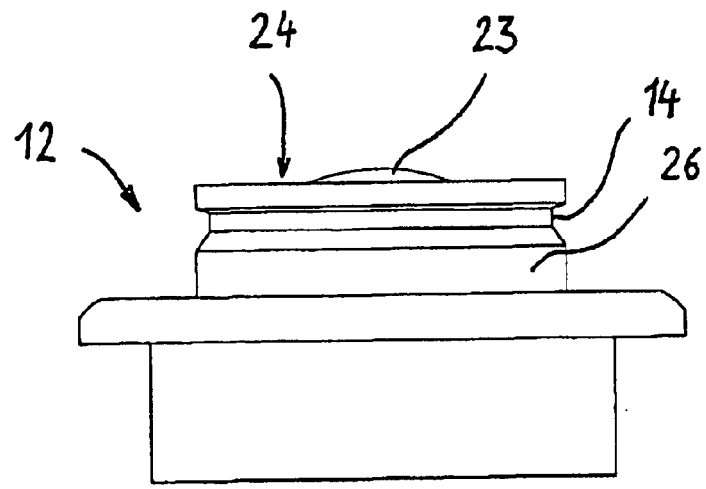
FIG. 2 shows a transducer according to the invention in side view.

The system element represented in FIG. 2 for the releasable sealed connection of a transducer to a fluid system in the form of a transducer 12 contains at least one sensor (not represented) for converting pressures and pressure changes into electrical signals, the sensor being arranged in a housing 26 and at least part of the housing 26 being filled with a fluid or gel which transmits pressure, and the housing 26 being closed by a transducer membrane 23 on one side, the housing 26 being further configured in the area 24 surrounding the transducer membrane 23 for applying a pressure dome 1, described further above, the surrounding area 24 essentially encompassing the transducer membrane 23 in a ring shape, and the measuring range of the sensor covering at least differential pressures with respect to the surroundings of −250 mm Hg to +1000 mm Hg, as far as possible down to differential pressures with respect to the surroundings of −350 mm Hg. It is preferred for the measuring range of the sensor to cover at least differential pressures with respect to the surroundings of −400 mm Hg to +3000 mm Hg.

The surrounding area 24 is approximately technically plane and the surface of the surrounding area 24 is smoothed to make it essentially free of scratches. The surface of the surrounding area 24 should have an averaged peak-to-valley height $R_z$ of no more than 20 $\mu$m, (for example in accordance with DIN 4768 Part 1) and/or a maximum peak-to-valley height $R_{max}$ of no more than 30 $\mu$m, preferably no more than approximately 20 $\mu$m.

The sealing effect required for the measurement of negative pressures can be obtained particularly reliably if the surrounding area 24 has a width of at least 2 mm.

When the pressure dome 1 and transducer 12 are put together (FIG. 3), the inclusion of even extremely small air cushions can be largely avoided, since the transducer membrane 23 is slightly pre-curved with respect to the area 24 surrounding it, for example by no more than 1 mm, preferably no more than 0.6 mm.

The transducer membrane 23 may be formed from an RTV silicone. It may also be advantageous for improving the long-term stability, however, if the transducer membrane 23 is formed from a polyurethane, preferably a TPE polyurethane. A coupling device for the mechanical connection of the pressure dome 1 and the transducer 12 may be formed by the hooks 13 and a corresponding undercut 14 on the transducer 12. However, other known coupling mechanisms also come into consideration, although a rotating movement between the membrane 11 and transducer membrane 23 should be avoided. For this purpose, it is possible for example for the hooks and undercut to be changed over. A different snap connection may also be provided, for example as proposed in WO 99/37983. Furthermore, bayonet connections, preferably with a screw collar ring, come into consideration, also correspondingly as a screw connection if excessive tightening of the connection is prevented by suitable spacers or the like. Finally, pivotably mounted clamps or toggle catches similar to closing hooks may also be provided.

When coupling has taken place (see FIG. 4), the membrane 11 of the pressure dome 1 is pressed in the area of the bead 20 against the area 24 surrounding the transducer membrane 23, so that an airtight seal takes place between the membrane 11 of the pressure dome 1 and the transducer 12; when coupling has taken place, the membrane 11 of the pressure dome 1 is pressed in the area of the bead 20 with at least 50 N, preferably by 90–110 N, against the area 24 surrounding the transducer membrane 23, and/or, once coupling has taken place, the membrane 11 of the pressure dome 1 is pressed together in the area of the bead 20 by approximately 0.1 mm to approximately 0.3 mm.

What is claimed is:

1. A system element for the releasable sealed connection of a transducer to a fluid system, with a measuring chamber (7) which can be connected to the fluid system in such a way as to allow throughflow, the measuring chamber (7) being formed in a housing (10) and part of the wall of the measuring chamber (7) being formed by a membrane (11) which is considerably more flexible than the rest of the wall (15) of the measuring chamber (7), characterized in that the membrane (11) has a peripheral bead (20) which is located on the side of the membrane (11) that faces toward the measuring chamber (7), the bead (20) engaging in a groove (19) which is formed in the housing (10) and extends around the measuring chamber (7) and the wall (inner wall 16) of the groove (19) that faces toward the measuring chamber (7) being lower than the wall (outer wall 17) of the groove (19) that faces away from the measuring chamber (7).

2. The system element as claimed in claim 1, characterized in that the difference in height of the outer wall (17) with respect to the inner wall (16) of the groove (19) is less than the average thickness of the membrane (11) in the area (21) outside the peripheral bead (20).

3. The system element as claimed in claim 1, characterized in that the membrane (11) protrudes at least approximately 0.1 mm, preferably at least approximately 0.3 mm, beyond the walls (16, 17) of the groove (19) in the area of the bead (20) after insertion of the bead (20) into the groove (19).

4. The system element as claimed in claim 1, characterized in that the membrane (11) is produced from an EPDM.

5. The system element as claimed in claim 1, characterized in that the membrane (11) is produced from a TPE.

6. The system element as claimed in claim 5, characterized in that the membrane (11) is produced from a TPE of the class SEBS.

7. The system element as claimed in claim 1, characterized in that the membrane (11) seals a negative pressure of 530 hPa with respect to air when a pressing pressure of 60 N is applied to a finely turned steel surface.

8. The system element as claimed in claim 1, characterized in that the membrane (11) has within the bead (20) a diameter of less than 12 mm.

9. The system element as claimed in claim 1, characterized in that the bead (20) has a width of approximately 2 mm in the longitudinal extent of the membrane (11).

10. The system element as claimed in claim 1, characterized in that the membrane (11) has within the bead (20) a thickness of approximately 0.4 mm to approximately 0.5 mm.

11. A system element for the releasable sealed connection of a transducer (12) to a fluid system, containing at least one sensor for converting pressures and pressure changes into electrical signals, the sensor being arranged in a housing (26) and at least part of the housing (26) being filled with a fluid or gel which transmits pressure, and the housing (26) being closed by a transducer membrane (23) on one side, the housing (26) being further configured in the area (24) surrounding the transducer membrane (23) for applying a system element as claimed in one of the preceding claims, the surrounding area (24) essentially encompassing the transducer membrane (23) in a ring shape, characterized in that the measuring range of the sensor covers at least differential pressures with respect to the surroundings of −250 mm Hg to +1000 mm Hg.

12. The system element as claimed in claim 11, characterized in that the measuring range of the sensor reaches at least down to differential pressures with respect to the surroundings of −350 mm Hg.

13. The system element as claimed in claim 12, characterized in that the measuring range of the sensor covers at least differential pressures with respect to the surroundings of −400 mm Hg to +3000 mm Hg.

14. The system element as claimed in claim 11, characterized in that the surrounding area (24) is approximately technically plane and the surface of the surrounding area (24) is smoothed to make it essentially free of scratches, preferably finely turned, ground or polished.

15. The system element as claimed in claim 11, characterized in that the surface of the surrounding area (24) has an averaged peak-to-valley height $R_Z$ of no more than 20 μm.

16. The system element as claimed in claim 11, characterized in that the surface of the surrounding area (24) has a maximum peak-to-valley height $R_{max}$ of no more than 30 μm, preferably no more than approximately 20 μm.

17. The system element as claimed in claim 11, characterized in that the transducer membrane (23) is slightly pre-curved with respect to the area (24) surrounding it.

18. The system element as claimed in claim 17, characterized in that the transducer membrane (23) is pre-curved with respect to the area surrounding it by no more than 1 mm, preferably no more than 0.6 mm.

19. The system element as claimed in claim 11, characterized in that the transducer membrane (23) is formed from an RTV silicone.

20. The system element as claimed in claim 11, characterized in that the transducer membrane (23) is formed from a polyurethane, preferably a TPE polyurethane.

21. The system element as claimed in claim 11, characterized in that the surrounding area (24) has a width of at least 2 mm.

22. A set comprising a system element as claimed in claim 1, characterized in that the system element is designed as a pressure dome (1).

23. The set as claimed in claim 22, characterized in that at least one coupling device (13, 14) for the mechanical connection of the pressure dome (1) and the transducer (12) is provided and the membrane (11) of the pressure dome (1) is pressed in the area of the bead (20) against the area (24) surrounding the transducer membrane (23), so that an airtight seal takes place between the membrane (11) of the pressure dome (1) and the transducer (12) when the pressure dome (1) and transducer (12) are coupled.

24. The set as claimed in claim 22, characterized in that, when coupling has taken place, the membrane (11) of the pressure dome (1) is pressed in the area of the bead (20) with at least 50 N, preferably by 90–110 N, against the area (24) surrounding the transducer membrane (23).

25. The set claimed in one of claims 22, characterized in that, once coupling has taken place, the membrane (11) of the pressure dome (1) is pressed together in the area of the bead (20) by approximately 0.1 mm to approximately 0.3 mm.

* * * * *